STRAWBERRY PLANT
Filed Dec. 29, 1972 3 Sheets-Sheet 1
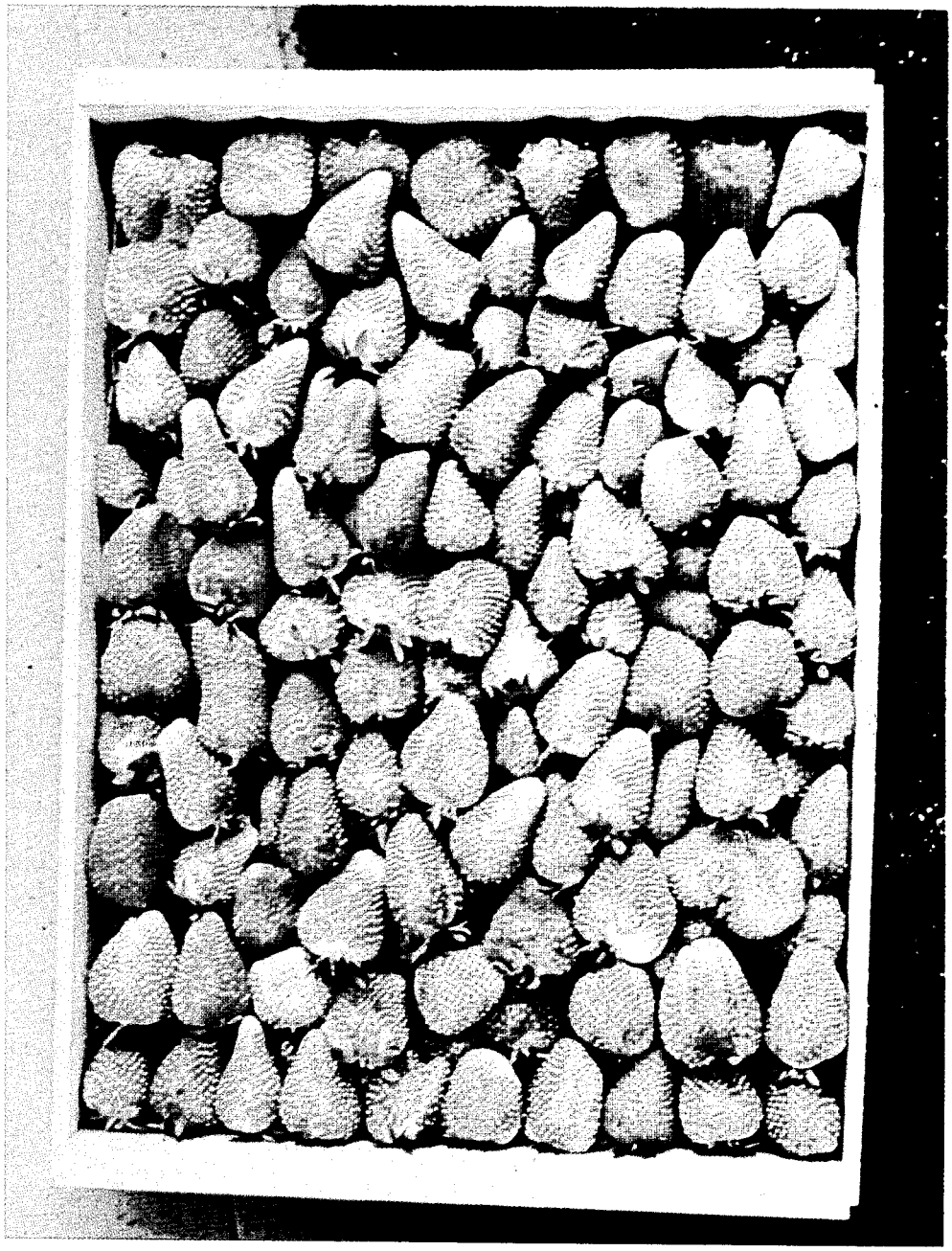

STRAWBERRY PLANT
Filed Dec. 29, 1972
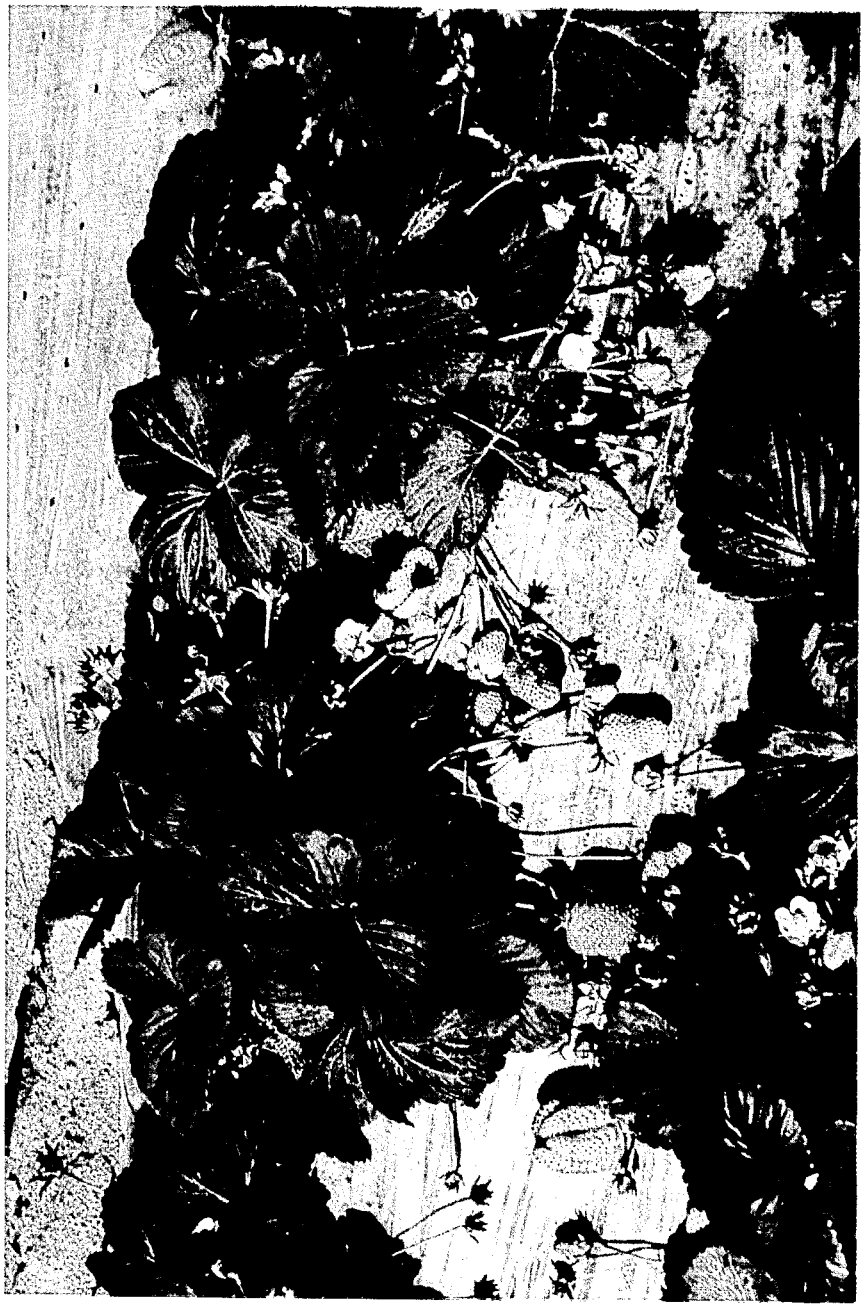

STRAWBERRY PLANT
Filed Dec. 29, 1972 3 Sheets-Sheet 3
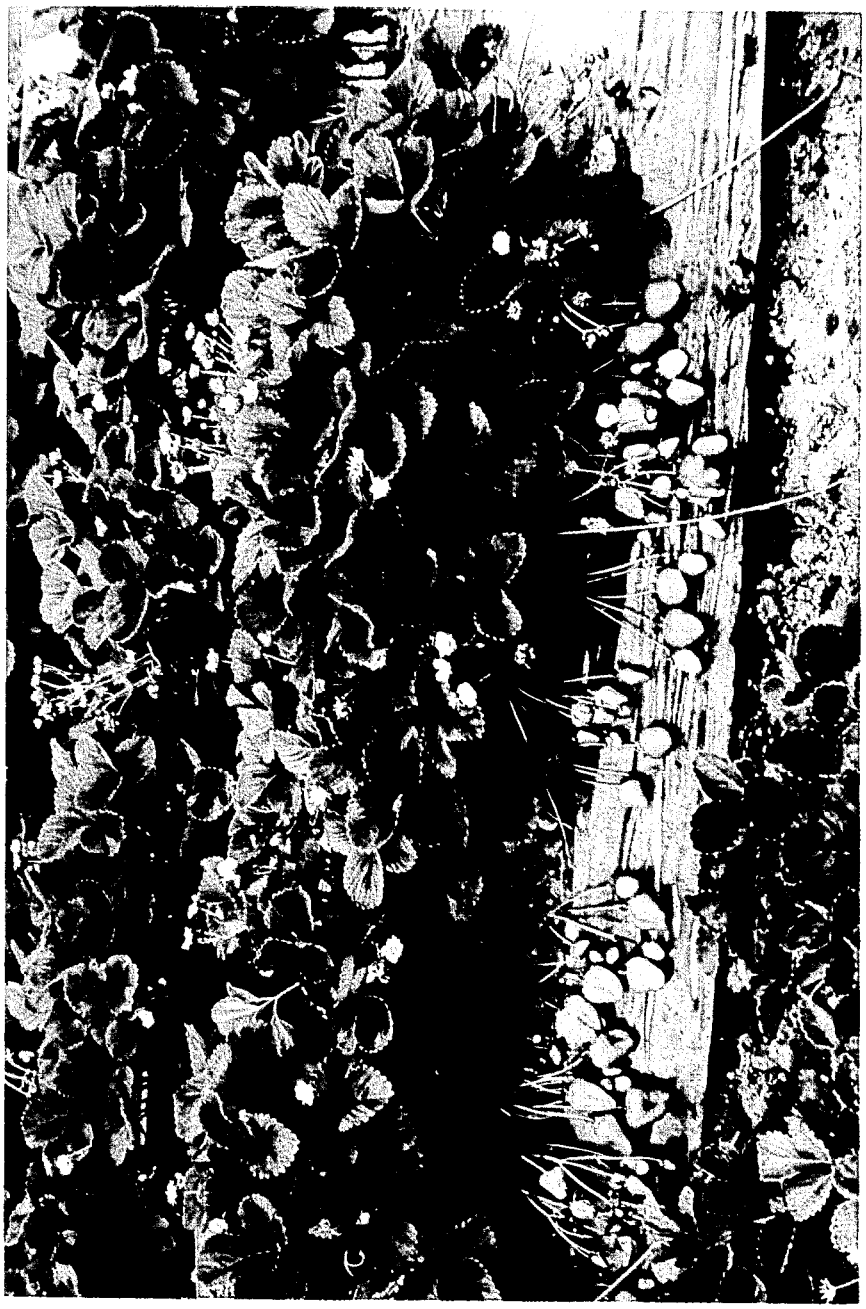

United States Patent Office

Plant Pat. 3,561
Patented June 4, 1974

3,561
STRAWBERRY PLANT

Royce S. Bringhurst, Davis, and Victor Voth, Santa Ana, Calif., assignors to The Regents of the University of California, Berkeley, Calif.

Filed Dec. 29, 1972, Ser. No. 319,275
Int. Cl. A01h *5/03*
U.S. Cl. Plt.—48 1 Claim This invention relates to a new and distinct variety of strawberry plant designated "Tufts" which is the result of a cross between two University of California selections, Cal 46.5–1 and "Tioga" (both unpatented).

The original "Tufts" seedling was fruited and selected at the South Coast Field Station of the University of California, Santa Ana, Calif., in 1965 and through asexual reproduction subsequently underwent testing in experimental plantings throughout California as Cal 63.120–11.

Typical plant, flower and fruit characteristics are presented in the accompanying color photographic reproductions:

FIG. 1 shows characteristic long conic shape of typical early fruit from winter planting in Southern California.

FIG. 2 shows characteristic leaf and plant growth habit typical of early winter planting in Southern California.

FIG. 3 shows typical springtime growth and fruiting habit of summer planting in the Central Coast area of California.

"Tufts" is a conventional short-day variety (noneverbearing) with cold and photoperiod conditioning requirements similar to those of "Tioga," although it consistently flowers and fruits earlier. Under a given cultural system, "Tufts" tends to fruit over a longer period of time than "Tioga," particularly under the summer planting system.

The plants are medium in size, similar in growth habit and appearance to those of "Tioga," but with a higher, more erect and somewhat less dense leaf canopy. The leaves are darker in color than those of "Tioga." The plants are slightly less vigorous and require a little more nitrogen than those of "Tioga," although not as much as those of "Shasta." Vigor may increase as virus-negative meristem stock becomes available. The plants have a relatively low chilling requirement and about as high a salinity tolerance as those of "Tioga." They are highly susceptible to Verticillium Wilt as are those of "Tioga," but they are less susceptible to leaf spot. The runners of the new variety are prolific in the nursery and the plant is much easier to propagate than "Tioga" since it roots better.

A most important distinguishing characteristic of the new variety is its adaptation to summer planting in all growing areas of California. Furthermore, "Tufts" can be planted as early as "Tioga" in a given area with good results and, in most coastal areas, can be planted successfully somewhat later than "Tioga." As a winter planting variety for coastal Southern California, "Tufts" is considered equally as successful as "Tioga."

The fruit of the new variety is distinct. It is relatively large in size, has a long conic shape which tends to be flat, and as the season advances the shape changes less than "Tioga." The fruit is attractive in appearance with generally even coloring and has a firmness which gives it superior transit and handling qualities. Other desirable features of the new variety are its high yield and desirable production pattern. More particularly, "Tufts" reaches its peak growth slower than "Tioga" and maintains a relatively level height after peaking, making it easy to harvest.

The dessert quality of the fruit is excellent in that it displays a pleasing combination of high sugar, subacidity and aroma.

VEGETATIVE AND FLORAL CHARACTERISTICS

Flowers are borne on long panicles that are positioned well above the leaf canopy until the weight of the ripening fruit brings it to the ground in an exposed position, clear of the basal leaves (much more so than "Tioga"). Thus, the ripened fruit tends to hang in an almost even line in full view. The flowers are self-fruitful and generally have an abundance of pollen. They tend to set well under a variety of conditions. However, some of the early fruit may be irregular due to incomplete pollination (similar to "Tioga").

FRUIT CHARACTERISTICS

Shape: Long, conic with tendency to be flat, particularly in the primaries. The long shape is held throughout the harvest system in contrast to "Tioga" which becomes almost round as the season advances. Most are slightly necked with a reflexed calyx.

Size: Relatively large, averaging about 21 grams.

Surface: About as tough as "Tioga." Seeds tend to be exposed giving a seedy appearance under certain conditions.

Color: Bright orange-red which deepens to a full red as the fruit ages, similar to "Tioga."

Flesh: Firm as long as the fruit does not get overripe on the plant. Internal color is a little more red than that of "Tioga."

Seeds: Medium to large size, yellow to reddish yellow, exposed on the surface.

Production: Heavy yield and desirable growth pattern, peaks more gradually than "Tioga" and maintains relatively level height.

Shipping: Excellent transit and handling qualities.

We claim:

1. A new and distinct strawberry variety described and illustrated, and characterized particularly by its adaptability to summer planting in all growing areas of California, its long conic fruit shape with a tendency to be flat, high productivity, desirable growth pattern, and excellent dessert, shipping and handling qualities.

No references cited.

ROBERT E. BAGWILL, Primary Examiner